United States Patent
Shibata et al.

(10) Patent No.: US 12,227,782 B2
(45) Date of Patent: Feb. 18, 2025

(54) METHOD FOR PRODUCING PROTEIN

(71) Applicant: Kao Corporation, Tokyo (JP)

(72) Inventors: Nozomu Shibata, Wakayama (JP); Toshiharu Arai, Wakayama (JP)

(73) Assignee: Kao Corporation, Tokyo (JP)

( * ) Notice: Subject to any disclaimer, the term of this patent is extended or adjusted under 35 U.S.C. 154(b) by 9 days.

(21) Appl. No.: 17/252,010

(22) PCT Filed: Jun. 27, 2019

(86) PCT No.: PCT/JP2019/025548
§ 371 (c)(1),
(2) Date: Dec. 14, 2020

(87) PCT Pub. No.: WO2020/008988
PCT Pub. Date: Jan. 9, 2020

(65) Prior Publication Data
US 2021/0254117 A1    Aug. 19, 2021

(30) Foreign Application Priority Data

Jul. 4, 2018   (JP) ................................ 2018-127519
Nov. 9, 2018   (JP) ................................ 2018-211690

(51) Int. Cl.
| C12N 1/38 | (2006.01) |
| C12N 1/14 | (2006.01) |
| C12N 9/24 | (2006.01) |
| C12P 21/00 | (2006.01) |

(52) U.S. Cl.
CPC ............... *C12P 21/00* (2013.01); *C12N 1/14* (2013.01); *C12N 9/2402* (2013.01); *C12Y 302/01004* (2013.01); *C12N 2500/34* (2013.01); *C12N 2500/60* (2013.01)

(58) Field of Classification Search
None
See application file for complete search history.

(56) References Cited

U.S. PATENT DOCUMENTS

| 6,326,477 B1 | 12/2001 | Ilmén et al. |
| 2008/0199908 A1 | 8/2008 | Smith et al. |
| 2018/0216121 A1 | 8/2018 | Arai et al. |
| 2020/0165647 A1 | 5/2020 | Kobayashi et al. |

FOREIGN PATENT DOCUMENTS

| CN | 101967501 A | 2/2011 |
| JP | H11-512930 A | 11/1999 |
| JP | 2015-039349 A | 3/2015 |
| WO | WO 2016/160956 A1 | 10/2016 |
| WO | WO 2017/007907 A1 | 1/2017 |
| WO | WO 2017/018471 A1 | 2/2017 |
| WO | WO 2017/170917 A1 | 10/2017 |

OTHER PUBLICATIONS

Jourdier et al. (Biotechnology for Biofuels, vol. 6, 79, 2013).*
International Search Report for PCT/JP2019/025548; I.A. fd Jun. 27, 2019, mailed Oct. 1, 2019 from the Japan Patent Office, Tokyo, Japan.
International Preliminary Report on Patentability (IPRP), Chapter I of the Patent Cooperation Treaty, including the Written Opinion, for PCT/JP2019/025548; I.A. fd Jun. 27, 2019, issued Jan. 5, 2021, by the International Bureau of WIPO, Geneva, Switzerland.
Ilmén M, et al., "Regulation of cellulase gene expression in the filamentous fungus *Trichoderma reesei*." Appl Environ Microbiol. Apr. 1997;63(4):1298-306. doi: 10.1128/AEM.63.4.1298-1306.1997. PMID: 9097427; PMCID: PMC168424.
Amore A, et al., "Regulation of cellulase and hemicellulase gene expression in fungi." Curr Genomics. Jun. 2013;14(4):230-49. doi: 10.2174/1389202911314040002. PMID: 24294104; PMCID: PMC3731814.
Hermann T, "Industrial production of amino acids by coryneform bacteria." J Biotechnol. Sep. 4, 2003;104(1-3):155-72. doi: 10.1016/s0168-1656(03)00149-4. PMID: 12948636.
Tian Y. et al., "pH Value Feedback Controlling of Carbon and Nitrogen Source Feeding in Lysine Fermentation," The Chinese Journal of Process Engineering 11(3): 402-406 (Jun. 2011).
Legler G., "Glycoside hydrolases: mechanistic information from studies with reversible and irreversible inhibitors." Adv Carbohydr Chem Biochem. 1990;48:319-84. doi: 10.1016/s0065-2318(08)60034-7. PMID: 2077872.
Komoto, M., "Chemical studies on the reaction products of glucose and ammonia, Part 1. Several changes of glucose in aqueous ammonia," Journal of the Agricultural Chemical Society of Japan 36:305-310 (1962).
Hrmová M. et al., "Growth of *Candida albicans* on artificial D-glucose derivatives." Z Allg Mikrobiol. 1983;23(5):303-12. PMID: 6353783.
Wayman M. et al., "Cellulase production by *Trichoderma reesei* using whole wheat flour as a carbon source." Enzyme and Microbial Technology vol. 14, Issue 10, Oct. 1992, pp. 825-831.
Nakazawa H., et al., Construction of a recombinant *Trichoderma reesei* strain expressing *Aspergillus aculeatus* β-glucosidase 1 for efficient biomass conversion. Biotechnol Bioeng. Jan. 2012; 109(1):92-9. doi: 10.1002/bit.23296. Epub Sep. 2, 2011. PMID: 21830204.
The extended European search report, including the supplementary European search report and the European search opinion for EP application No. 19830878.5, mailed May 11, 2022 from the European Patent Office, Munich, Germany.

* cited by examiner

*Primary Examiner* — Richard G Hutson
(74) *Attorney, Agent, or Firm* — Sterne, Kessler, Goldstein & Fox P.L.L.C.

(57) ABSTRACT

Provided is an inexpensive and efficient microbiological method for producing a protein. The method for producing a protein comprises culturing a microorganism in the presence of glycosylamine.

14 Claims, 1 Drawing Sheet
Specification includes a Sequence Listing.

[Figure 1]
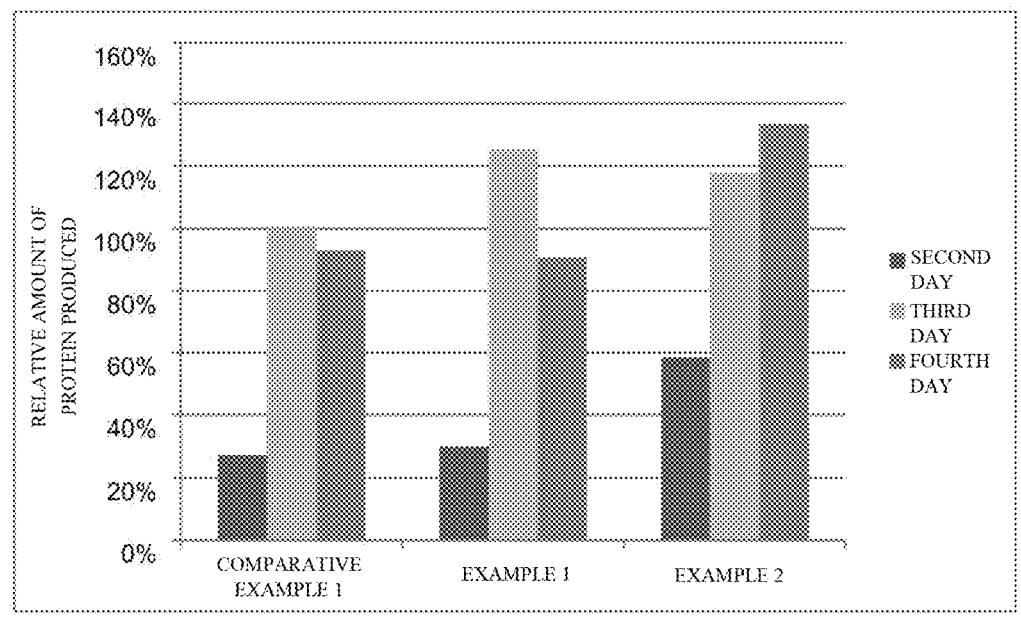
[Figure 2]
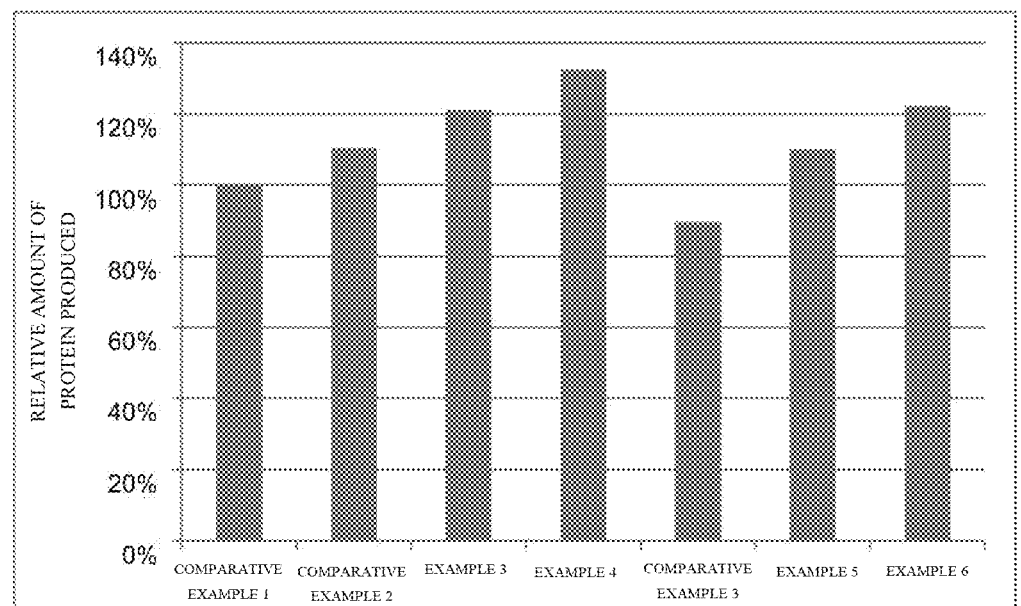

SEQUENCE LISTING

```
<160> NUMBER OF SEQ ID NOS: 3

<210> SEQ ID NO 1
<211> LENGTH: 1640
<212> TYPE: DNA
<213> ORGANISM: Trichoderma reesei
<220> FEATURE:
<223> OTHER INFORMATION: cbh1 promoter

<400> SEQUENCE: 1
tgcaaagttt tgtttcggct acggtgaaga actggatact tgttgtgtct tctgtgtatt      60
tttgtggcaa caagaggcca gagacaatct attcaaacac caagcttgct cttttgagct     120
acaagaacct gtggggtata tatctagagt tgtgaagtcg gtaatcccgc tgtatagtaa     180
tacgagtcgc atctaaatac tccgaagctg ctgcgaaccc ggagaatcga gatgtgctgg     240
aaagcttcta gcgagcggct aaattagcat gaaaggctat gagaaattct ggagacggct     300
tgttgaatca tggcgttcca ttcttcgaca agcaaagcgt tccgtcgcag tagcaggcac     360
```

| | | |
|---|---|---|
| tcattcccga aaaaactcgg agattcctaa gtagcgatgg aaccggaata atataatagg | 420 | |
| caatacattg agttgcctcg acggttgcaa tgcaggggta ctgagcttgg acataactgt | 480 | |
| tccgtacccc acctcttctc aacctttggc gtttccctga ttcagcgtac ccgtacaagt | 540 | |
| cgtaatcact attaacccag actgaccgga cgtgttttgc ccttcatttg agaaataat | 600 | |
| gtcattgcga tgtgtaattt gcctgcttga ccgactgggg ctgttcgaag cccgaatgta | 660 | |
| ggattgttat ccgaactctg ctcgtagagg catgttgtga atctgtgtcg ggcaggacac | 720 | |
| gcctcgaagg ttcacggcaa gggaaaccac cgatagcagt gtctagtagc aacctgtaaa | 780 | |
| gccgcaatgc agcatcactg gaaaatacaa accaatggct aaaagtacat aagttaatgc | 840 | |
| ctaaagaagt catataccag cggctaataa ttgtacaatc aagtggctaa acgtaccgta | 900 | |
| atttgccaac ggcttgtggg gttgcagaag caacggcaaa gccccacttc cccacgtttg | 960 | |
| tttcttcact cagtccaatc tcagctggtg atcccccaat tgggtcgctt gtttgttccg | 1020 | |
| gtgaagtgaa agaagacaga ggtaagaatg tctgactcgg agcgttttgc atacaaccaa | 1080 | |
| gggcagtgat ggaagacagt gaaatgttga cattcaagga gtatttagcc agggatgctt | 1140 | |
| gagtgtatcg tgtaaggagg tttgtctgcc gatacgacga atactgtata gtcacttctg | 1200 | |
| atgaagtggt ccatattgaa atgtaagtcg gcactgaaca ggcaaaagat tgagttgaaa | 1260 | |
| ctgcctaaga tctcgggccc tcgggccttc ggcctttggg tgtacatgtt tgtgctccgg | 1320 | |
| gcaaatgcaa agtgtggtag gatcgaacac actgctgcct ttaccaagca gctgagggta | 1380 | |
| tgtgataggc aaatgttcag gggccactgc atggtttcga atagaaagag aagcttagcc | 1440 | |
| aagaacaata gccgataaag atagcctcat taaacggaat gagctagtag gcaaagtcag | 1500 | |
| cgaatgtgta tatataaagg ttcgaggtcc gtgcctccct catgctctcc ccatctactc | 1560 | |
| atcaactcag atcctccagg agacttgtac accatcttt gaggcacaga aacccaatag | 1620 | |
| tcaaccgcgg actgcgcatc | 1640 | |

<210> SEQ ID NO 2
<211> LENGTH: 1477
<212> TYPE: DNA
<213> ORGANISM: Trichoderma reesei
<220> FEATURE:
<223> OTHER INFORMATION: egl1 promoter

<400> SEQUENCE: 2

| | | |
|---|---|---|
| tttcagcaat gcgtggcgtt ggcaggcgac ttcgcggcag tgcatgagcg atattcgggg | 60 | |
| tcgttgaagc cgacgttcac gccggagatt ggcatgatcc cagtgcttta catcatcggg | 120 | |
| gccaaatgcc ggcatcctgt tgtgcggcgg gaggccttgg gtcttttgag gcggcaaccg | 180 | |
| atccgggagg cggtttggga tagcgttgtt gttgccaggg tagtggagag gataatggag | 240 | |
| attgaggagg ttgggtttga gaagtgggaa atgatacaga gtatggaaca ggttccggtg | 300 | |
| tggcagaggg ttgagacgct gtcttgggca catgtcgtcg tcgatggaca gtctgcgggc | 360 | |
| agagtggaca ttaactatac gttctgcgcg cgagagggat cgcatattga gtctttcatg | 420 | |
| atgtaataag cttgggcttg acagcgttct attgccagtg tatcaacgaa gtggtatgta | 480 | |
| ccatcgtgct ctgtccagac gttttggtca ggtcgacaaa caggcttttc ttcctattct | 540 | |
| ctttctttga tatatacacg cttagaaatg tgtcaaaaag aacagaaacc tcttttgatg | 600 | |
| tagttatgcg catgctagac tgctcctgtt tcatgtggtt acaacaaaca gtctgatcga | 660 | |
| cttcgaatac ttggactgat gaaggttgta cagattgctg acagatgtcg taatgcagag | 720 | |
| caaggctgta gattccataa aaccagttgc ttcgcctgct gtggctctgg agaaccaaag | 780 | |

-continued

```
agacgtgtct cgggagggta agtggtatcg aatctatgag agaagcccag tctaagagag      840
gaccatctcg ccaggggaag atgaagctgg ttacaactga tttgttttcc cgtctgccac      900
catggtatag agcctggacc aatcaggcta aatcattgta tacaataagc ctagagaaaa      960
cctgaaatct gtcctcgtcc tttgtccgtt gtctaattat ccgttatttt cgaacgatga     1020
tacagtatga gttttgccga aattttgcta aaggtactat cgacggggga cacaagggtt     1080
gagtctgtat aacggctcga aacagcagct ggtagcagga atccaggccc gcgtttcatt     1140
tggattcatt ttcccatatt ccccttgcag aaggatacga cagtagcatt ggaaaccgta     1200
aatgacggca aaaagcatgg ttctgctcag atactccaag ccaacctatc gggtcctgga     1260
ggctatttcc aacatctcat agcctaacag aaataacgga agtcggcatc tgtatcgctc     1320
aaactgacca gacgagcccg ccatatcgag gcagagttac tctgtgttgc aaatccaact     1380
tataaagaca acaaccgcaa actttgtctt gtcgccatca gattgttcgc caagcaccct     1440
cccccccccc tatcttagtc cttcttgttg tcccaaa                              1477
```

<210> SEQ ID NO 3
<211> LENGTH: 1084
<212> TYPE: DNA
<213> ORGANISM: Trichoderma reesei
<220> FEATURE:
<223> OTHER INFORMATION: xyn3 promoter

<400> SEQUENCE: 3

```
gggaattccg tgattgacaa aatctattcg tatcaaacgt tcatgccgcc gtctccagtc       60
tcctcacgct atggtgcttg atatacataa gggggggacg ttgaatatat gttcccagtt      120
tacctccaca taagaaatat ctcctttgga cggtctctgc aattttgccc tcaagactct      180
gcagacaatc cctctgtgct ttaaaacccc cgagtatccc ggtcacctga tggcgcaagt      240
ctcaacttcc ccaggatgcc gtctcctcat ctccgtgatg gtaacaaccg catataaggg      300
acttttgtct tctttaggct tcggacgagg gggttctttc ccagatcaat gccttgaccg      360
aaactgtcaa gatggctata taggacactg tcaattttgc catttcagtc cgggtattta      420
gacttaaaag cacctagtat ttatggttaa taaatctccg ggcaaaggtc tctttccgtg      480
cgtgtctgat gggttatgct aagctcatct ccgcagacag ggtagtaaca gaggtagccg      540
ttccttggaa agacggttaa ttgacttctt gactttgact gtccaattcg catggctaat      600
tgcggcaaaa atgatgccat atggccccgt gggcacaact ttctcacaag tctctggtgt      660
cttgactgag gtcgatgttg tgctctttct tcccaactat acaagtctaa actcctcagt      720
aaatcgatac aaggtaaatt taaactctct ggttactctt cctaccaaaa ggccctggtt      780
acatttcgtg tatacccgag gcggctgaat ctggggact cacataggtg gatgcaatgt      840
gctattagcc agctacgcat atacaatcaa acattgaaaa tcaaaggata tacaacaact      900
ttgacgattt tccataaatt ggcatcatct ttctgagtcc tgatggatgt cagacagcaa      960
gcggacaagc tggctcatga ctcaatcctc cgaatacatc gcatcatcta ggagccattc     1020
tcacctcgaa acttctacca tctttccact gagtttcaat tgaggcggac accatggaag     1080
cacc                                                                 1084
```

METHOD FOR PRODUCING PROTEIN

FIELD OF THE INVENTION

The present invention relates to a method for producing a protein using a microorganism.

BACKGROUND OF THE INVENTION

Filamentous fungi produce various cellulases and xylanases, and draw attention as plant polysaccharide-degrading fungi. In particular, *Trichoderma* is capable of producing a cellulase and xylanase at a time in large amounts, and is being studied as a microorganism for producing a cellulase-based biomass-degrading enzyme. In culture of microorganisms, glucose has been heretofore commonly used as a carbon source. However, when glucose is present, a control mechanism called catabolite repression causes reduction or saturation of substance productivity of microorganisms. Wide domain transcription factors CreA, CreB, CreC, CreD and the like have been reported to be involved in catabolite repression of filamentous fungi such as *Aspergillus* (Patent Literature 1). It may be possible to regulate catabolite repression of *Aspergillus* by control of these transcription factors, but adequate results have not been obtained yet. For *Trichoderma*, analysis of the mechanism of catabolite repression has been proceeding (Patent Literature 2 and Non Patent Literature 1). However, much of the mechanism of catabolite repression of *Trichoderma* is still unclear, and avoidance of repression has not been achieved.

Production of protein such as an enzyme by a microorganism may require an inducing substance in addition to carbon sources. For example, expression of an alpha-amylase gene of *Aspergillus oryzae* is induced by starch, maltose and the like. Expression of main cellulase genes cbh1, cbh2, egl1 and egl2 of *Trichoderma* is induced by cellulose, cellobiose and the like (Non Patent Literature 2). Starch, maltose, cellulose and cellobiose can also be used as carbon sources for culturing. In production of cellulase using a microorganism, microcrystalline cellulose such as Avicel is generally used.

Patent Literature 3 discloses a method for producing a cellulase by a microorganism using lignocellulose instead of pure cellulose as an inducing substance. In Patent Literature 3, a cellulase is produced by culturing *Trichoderma* with glucose fed as a carbon source and phosphoric acid or ammonia water fed as a pH adjuster in a culture medium containing a cellulose-based material. Non-Patent Literature 3 discloses that an amino acid was produced by *Corynebacterium* with saccharides repeatedly or continuously fed to a culture medium. Patent Literature 4 and Non Patent Literature 4 disclose that lysine was fermentatively produced by feeding a mixed solution of glucose and ammonia to a culture, and adding a carbon source and a nitrogen source while controlling the pH value, and that this method increased the productivity of lysine.

Glycosylamine is a monosaccharide derivative in which the hydroxy group at position C-1 is substituted with an amino group. Glycosylamine is often synthesized and used as an intermediate for various saccharide derivatives. β-D-glycosylamine has been reported to act as a β-glycosidase inhibitor (Non Patent Literature 5). Non Patent Literature 6 discloses that β-D-glucosylamine is generated through reaction of glucose with ammonia. Non Patent Literature 7 discloses that various D-glucose derivatives containing β-D-gluocopyranosylamine were able to be used as carbon sources for hyphal growth of *Candida albicans*.

[Patent Literature 1] JP-A-2015-39349
[Patent Literature 2] JP-A-11-512930
[Patent Literature 3] US 2008/0199908A
[Patent Literature 4] CN 101967501C Non Patent Literature

[Non Patent Literature 1] Appl. Environ. Microbiol., 63: 1298-1306 (1997)
[Non Patent Literature 2] Curr. Genomics, 14: 230-249 (2013)
[Non Patent Literature 3] Journal of Biotechnology, 104: 155-172 (2003)
[Non Patent Literature 4] The Chinese Journal of Process Engineering, 11(3): 492-496 (2011)
[Non Patent Literature 5] Adv. Carbohydr. Chem. Biochem., 48: 319-384 (1990)
[Non Patent Literature 6] Journal of the Agricultural Chemical Society of Japan, 36: 305-310 (1962)
[Non Patent Literature 7] Journal of Basic Microbiology, 23(5): 303-312 (1983)

SUMMARY OF THE INVENTION

The present invention provides a method for producing a protein, comprising culturing a microorganism in the presence of glycosylamine.

BRIEF DESCRIPTION OF THE DRAWINGS

FIG. 1 shows the relative amounts of protein produced of cultures. Each value is a relative value on day 2, day 3 or day 4 of culture against the amount of protein produced on day 3 of culture in Comparative Example 1, which is defined as 100%.

FIG. 2 shows the relative amounts of protein produced of cultures. Each value is a relative value against the amount of protein produced on day 3 of culture in Comparative Example 1, which is defined as 100%.

DETAILED DESCRIPTION OF THE INVENTION

All patent documents, non-patent documents and other publications cited herein are incorporated herein by reference in their entirety.

As used herein, the "upstream" and the "downstream" with respect to a gene means upstream and downstream in a transcription direction of the gene. For example, the "gene located downstream of a promoter" means that the gene is present on the 3' side of the promoter in a DNA sense strand, and the upstream of the gene means a region on the 5' side of the gene in the DNA sense strand.

As used herein, the "operable linkage" between a promoter and a gene means that the promoter and the gene are linked in such a manner that the promoter can induce transcription of the gene. The procedure for "operable linkage" between a promoter and a gene is well known to persons skilled in the art.

As used herein, the "promoter activity" means activity of promoting expression of a gene located downstream of the promoter, more specifically activity of promoting transfer of a gene located downstream of the promoter from DNA to mRNA.

As used herein, the term "intrinsic" which is used in connection with functions, properties and traits of cells is used to indicate that the functions, properties and traits are inherent in the cells. In contrast, the term "foreign" is used to indicate functions, properties and traits which are not inherent in the cells, but are introduced from the outside. For example, the "foreign" gene or polynucleotide is a gene or polynucleotide introduced into cells from the outside. The foreign gene or polynucleotide may be one derived from an organism identical in species to cells into which the foreign gene or polynucleotide has been introduced, or one derived from an organism different in species from the cells (i.e., a heterologous gene or polynucleotide)

As used herein, the "identity of at least 90%" in connection with an amino acid sequence or a nucleotide sequence means an identity of 90% or more, preferably 95% or more, more preferably 96% or more, even more preferably 97% or more, even more preferably 98% or more, even more preferably 99% or more.

As used herein, the identity of a nucleotide sequence and an amino acid sequence is calculated by the Lipman-Pearson method (Science, 1985, 227: 1435-1441). Specifically, the identity is calculated by performing analysis with a unit size to compare (ktup) of 2 by using the homology analysis (Search homology) program of gene information processing software Genetyx-Win.

Development of an inexpensive and efficient culture technique for producing a protein such as an enzyme by a microorganism is required. By fed-batch culture in which glucose is repeatedly or continuously fed to a culture, catabolite repression may be suppressed to improve the productivity of protein by a microorganism. However, when the amount of glucose is small, the protein synthesis process does not sufficiently proceed. On the other hand, feeding of a large amount of glucose causes catabolite repression. Therefore, in production of protein by glucose fed-batch culture, precise control of the glucose concentration in a culture is required.

The present inventors found that culture of a microorganism in the presence of glycosylamine improves the productivity of protein such as an enzyme by the microorganism.

According to the present invention, it is possible to improve the productivity of protein by a microorganism in a convenient procedure.

The method for producing a protein according to the present invention comprises culturing a microorganism in the presence of glycosylamine. Examples of glycosylamine for use in the present invention include β-D-glucopyranosylamine (CAS No. 7284-37-9), β-D-mannopyranosylamine (CAS No. 7388-99-0) and β-D-galactopyranosylamine (CAS No. 74867-91-07), and one of these glycosylamines may be used alone, or two or more thereof may be used in combination. Glycosylamine for use in the present invention is preferably β-D-glucopyranosylamine, which is a compound in which the hydroxy group at position C-1 in β-D-glucose is substituted with an amino group. Glycosylamine is available in the market, or can be produced in accordance with the procedure described in J. Org. Chem, 1958, 23(9): 1309-1319.

In one embodiment of the method of the present invention, a microorganism is cultured in a culture medium containing glycosylamine. In an example, glycosylamine is added to an initial culture medium for culturing, and a microorganism is cultured using the culture medium. The amount of glycosylamine added to the initial culture medium is preferably 50 g or less, more preferably 30 g or less, even more preferably from 0.5 to 20 g, even more preferably from 1 to 10 g per L of the initial culture medium. In another example, glycosylamine is fed to a microbial culture. The amount of glycosylamine fed to the culture is preferably 5 g/hr or less, more preferably 4 g/hr or less, even more preferably from 0.005 to 4 g/hr, even more preferably from 0.01 to 3 g/hr per L of the initial culture medium. Alternatively, addition of glycosylamine to the initial culture medium may be combined with feeding of glycosylamine to the culture. In this case, it is preferable to adjust the amount of glycosylamine added to the initial culture medium and the amount of glycosyl amine fed so that the content of glycosylamine in the culture is preferably from 0.5 to 50 g, more preferably from 0.5 to 20 g, even more preferably from 1 to 10 g per L of the culture. Feeding may be intermittent, or the feeding rate may be varied. Conditions for feeding are determined in consideration of the productivity of protein.

When glycosylamine is fed to a microbial culture in the method of the present invention, it is preferable that an aqueous solution containing glycosylamine be fed to the culture. The content of glycosylamine in the aqueous solution is preferably from 2 to 90 mass %, more preferably from 2 to 50 mass %. When the amount of glycosylamine in the aqueous solution is excessively small, a large amount of the aqueous solution is fed to the culture, so that culture equipment is overloaded. On the other hand, when the amount of glycosylamine in the aqueous solution is excessively large, it is difficult to control the amount of the aqueous solution fed to the culture.

The aqueous solution containing glycosylamine may be an aqueous solution obtained by directly adding glycosylamine to water and dissolving the glycosylamine in the water, or a mixture of glucose and ammonia (which contains glycosylamine generated by reaction of glucose with ammonia; see Non Patent Literature 6). Therefore, as one embodiment, the method of the present invention can include culturing a microorganism while feeding a mixture of glucose and ammonia. The mixture of glucose and ammonia is a liquid mixture prepared by mixing glucose and ammonia. For example, the mixture is a mixture of glucose, ammonia and a solvent thereof (e.g. water). Preferably, the mixture is a mixture prepared by mixing glucose or an aqueous solution thereof, and ammonia, a salt thereof or an aqueous solution thereof, and water if necessary. More preferably, the mixture is a mixture obtained by mixing glucose, and an ammonia aqueous solution, and water if necessary. In preparation of the mixture of glucose and ammonia, glucose and ammonia may be mixed at a mass ratio of preferably from 0.5 to 10:1, more preferably from 2 to 8:1. When the ratio of glucose is excessively high, cells tend to make a transition from an enzyme-producing state to a growing state, leading to reduction of the enzyme productivity. On the other hand, when the ratio of glucose is excessively low, the amount of carbon source is insufficient, and resultantly, improvement in the enzyme productivity cannot be expected. In preparation of the mixture of glucose and ammonia, the amount of glucose added may be adjusted to preferably from 2 to 90 g, more preferably from 5 to 80 g per 100 mL of the resulting mixture. When the amount of glucose added to the mixture is excessively small, a large amount of the mixture is fed to the culture for achieving the above-described amount of glycosylamine fed, so that culture equipment is overloaded. On the other hand, when the amount of glucose added to the mixture is excessively large, it is difficult to control the amount of the mixture fed to the culture. For example, the mixture may be prepared by mixing an appropriate amount of glucose and an ammonia aqueous solution so as to enable achievement of the above-described ratio of glucose to ammonia and/or amount of glucose added, or may be prepared by mixing an arbitrary amount of glucose and an ammonia aqueous solution, and then appropriately diluting the resulting mixture with water so as to enable achievement of the above-described ratio of glucose to ammonia and/or amount of glucose added.

When the mixture of glucose and ammonia is fed to a microbial culture, the amount of the mixture fed to the culture may be an amount enabling the amount of glycosylamine fed to fall within the above-described range, and is, for example, preferably 8 g/hr or less, more preferably 6 g/hr or less, even more preferably from 0.05 to 8 g/hr, even more preferably from 0.1 to 6 g/hr per L of an initial culture medium (culture medium free from the mixture fed) in terms of the amount of glucose added to the mixture. When the amount of glucose fed is large, catabolite repression may occur. On the other hand, the amount of the (entire) mixture fed to the culture may be appropriately adjusted according to the content of the glucose or ammonia, or the pH of the culture as described below, and is not particularly limited. From the viewpoint of economic efficiency, the amount of the (entire) mixture fed may be adjusted to about from 0.1 to 10 g/hr, preferably about from 0.3 to 8 g/hr per L of an initial culture medium.

Preferably, the pH of the culture is adjusted by feeding the mixture of glucose and ammonia. In this case, the amount of the mixture fed and the timing of feeding the mixture depend on the pH of the culture to which the mixture is fed. Suitably, an initial culture medium with a predetermined pH is prepared in a usual procedure, followed by culturing while the mixture of glucose and ammonia is fed in such a manner that the culture after being fed maintains the predetermined pH value. While it is preferable to use only the mixture of glucose and ammonia for adjustment of the pH of the culture during culture, another pH adjuster may be used in combination. Measurement of the pH of the culture and control of the amount fed based on the pH value can be performed using a commercially available jar fermenter or the like. The pH of the culture can be set to an appropriate value according to the species of organism, and the type of protein to be produced. For example, when the microorganism is filamentous fungi, the culture is maintained at a pH of preferably from 3 to 7, more preferably from 3.5 to 6. In general, the pH of the culture can be measured with an electrode provided in a jar fermenter. Suitably, the pH of the culture in the present invention is a value measured with a pH sensor such as F-635 Autoclavable pH Electrode (Broadley-James Corp) or 405-DPAS-SC-K8S pH sensor (METTLER TOLEDO) at a culture temperature of 28° C.

The pH of the aqueous solution containing glycosylamine is preferably an alkaline pH, more preferably 8 or more, even more preferably 9 or more, even more preferably 10 or more, and preferably 13 or less at 25° C., from the viewpoint of the stability of glycosylamine. When the aqueous solution containing glycosylamine is the above-described mixture of glucose and ammonia, the pH of the mixture of glucose and ammonia is preferably an alkaline pH, more preferably 8 or more, even more preferably 9 or more, even more preferably 10 or more, and preferably 13 or less at 25° C. Preferably, the pH of the aqueous solution containing glycosylamine is adjusted to be within the above-described range using a pH adjuster such as an alkaline agent (e.g. ammonia) if necessary. The pH of the aqueous solution containing glycosylamine can be measured using a common pH meter. For example, a pH measuring composite electrode (e.g. Ground Glass Sleeve Type manufactured by HORIBA, Ltd.) connected to a pH meter (pH/Ion Meter F-52 manufactured by HORIBA, Ltd.) is used. A saturated potassium chloride aqueous solution (3.33 mol/L) is used as a pH electrode internal liquid. The measurement is performed at 25° C.

The aqueous solution containing glycosylamine may further contain other substances which can be typically added to a microbial culture medium. Examples of the other substances include organic salts, inorganic salts, pH adjusters, carbon sources and nitrogen sources other than glycosylamine, surfactants, and defoaming agents. It is preferable to use glucose in combination as a carbon source, and it is preferable to use ammonia as a nitrogen source. Ammonia can also be used as a pH adjuster. One or more selected from glucose and ammonia may be partially or wholly contained in an initial culture medium, or may be fed. When one or more of glucose and ammonia are fed, the feeding rate of the aqueous solution containing the one or more of glucose and ammonia is preferably a feeding rate at which the total amount of glycosylamine, glucose and ammonia fed does not exceed the above-described amount of glycosylamine fed. Preferably, the total amount of glucose, ammonia and glycosylamine in the initial culture medium and the culture does not exceed the above-described content of glycosylamine in the initial culture medium and the culture.

The mixture of glucose and ammonia may further contain other substances which can be typically added to a microbial culture medium. The other substances are preferably substances which do not impair the pH adjustment function of the mixture, and examples thereof include organic salts, inorganic salts, other pH adjusters, carbon sources and nitrogen sources other than glucose and ammonia, surfactants, and defoaming agents.

In the present invention, the initial culture medium used for culturing a microorganism may be a culture medium which is commonly used for culturing the microorganism. For example, the initial culture medium may contain various components which are generally contained in microbial culture media, such as carbon sources, nitrogen sources, metal salts such as magnesium salts and zinc salts, sulfates, phosphates, pH adjusters, surfactants and defoaming agents. The composition of components in the culture medium can be appropriately selected. The initial culture medium may be any of a synthetic culture medium, a natural culture medium and a semisynthetic culture medium, or may be a commercially available culture medium. The initial culture medium is preferably a liquid culture medium.

Preferably, a microorganism is cultured in the presence of a substance which induces expression of a gene encoding a target protein in the method of the present invention. This enables further enhancement of the productivity of target protein. More specifically, the microbial culture may contain the inducing substance. For example, the inducing substance may be contained in the initial culture medium, fed to the culture, or both contained and fed. Preferred examples of the inducing substance include cellulose and cellobiose, and one or both thereof can be used. Cellulose or cellobiose in the culture can be consumed as a carbon source while acting as an inducing substance. The concentration of cellulose or cellobiose in the culture is preferably from 1 to 15 mass/vol % as a total concentration of cellulose and cellobiose. For example, when cellulose or cellobiose is added to the initial culture medium, the concentration of cellulose or cellobiose in the initial culture medium is preferably from 1 to 15 mass/vol % as a total concentration of cellulose and cellobiose. It is known that expression of a cellulase gene of filamentous fungi such as *Trichoderma* is induced by cellulose, cellobiose or the like, and catabolite repression is caused by glucose (Patent Literature 2 and Non Patent Literatures 1 and 2). Therefore, the method of the present invention using the inducing substance can be suitably used for production of a cellulase using filamentous fungi.

Alternatively, a gene encoding a target protein is linked to a promoter which is induced by cellulose or cellobiose, such as a promoter of a gene encoding cellulase of filamentous fungi (so called a cellulase gene promoter of filamentous fungi), whereby expression of a gene of the target protein can be induced by cellulose or cellobiose. Therefore, in a preferred embodiment of the method of the present invention, the microorganism is cultured in the presence of at least one selected from the group consisting of cellulose and cellobiose, the microorganism contains a promoter which is induced by cellulose or cellobiose, and a gene encoding a target protein is operably linked downstream of the promoter.

Examples of the promoter which is induced by cellulose or cellobiose include promoters of cellulase genes or xylanase genes of filamentous fungi. Examples of the promoters of cellulase genes of filamentous fungi include promoters of cellulase genes of *Trichoderma* fungi, and preferred examples thereof include promoters of cellulase genes of *Trichoderma reesei* which consist of a nucleotide sequence of SEQ ID NO: 1 or 2. Examples of the promoters of xylanase genes of filamentous fungi include promoters of xylanase genes of *Trichoderma* fungus, and preferred examples thereof include promoters of xylanase genes of *Trichoderma reesei* which have a nucleotide sequence of SEQ ID NO: 3. Further examples of the promoters which are induced by cellulose or cellobiose include polynucleotides consisting of a nucleotide sequence with an identity of at least 90% to any of the nucleotide sequences of SEQ ID NOS: 1 to 3 and having promoter activity induced by cellulose or cellobiose.

The promoter may be a promoter intrinsic to a microorganism cultured in the method of the present invention, or a foreign promoter introduced into the microorganism. Linkage of such a promoter to a gene encoding a target protein can be performed in accordance with a known procedure such as a restriction enzyme method or a homologous recombination method. For example, a vector or DNA fragment having a polynucleotide containing a gene encoding a target protein is introduced into microbial cells, and the polynucleotide is incorporated downstream of a target promoter in a genome, whereby the promoter and the gene encoding the target protein are operably linked on the genome. Alternatively, a vector or DNA fragment having a promoter sequence and a polynucleotide containing a gene encoding a target protein linked downstream of the promoter sequence may be constructed, and introduced into microbial cells. If necessary, the vector or DNA fragment may further have selection markers such as antibiotic resistance genes and auxotrophy-related genes.

The vector may be a vector capable of autonomously proliferating and replicating outside a chromosome such as a plasmid, or may be a vector which is incorporated in a chromosome. The preferred type of vector depends on the species of a microorganism into which the vector is introduced. Preferred examples of the vector for filamentous fungi include, but are not limited to, plasmids containing AMA1 which act as an autonomous replication factor in *Aspergillus* microorganisms.

For introduction of the vector or DNA fragment into a microorganism, a general transformation method can be used, such as an electroporation method, a transformation method, a transfection method, a conjugation method, a protoplast method, a particle gun method or an *agrobacterium* method.

A microorganism having a target vector or DNA fragment introduced therein can be selected by using a selection marker. For example, when the selection marker is an antibiotic resistance gene, a microorganism having a target vector or DNA fragment introduced therein can be selected by culturing the microorganism in a culture medium containing the antibiotic. For example, when the selection marker is an auxotrophy-related gene such as an amino acid synthesis-related gene or a base synthesis-related gene, the gene is introduced into a host having the auxotrophy, followed by using existence or non-existence of the auxotrophy as an index to thereby select a microorganism having a target vector or DNA fragment introduced therein. Alternatively, the DNA sequence of a microorganism can be examined by PCR or the like to confirm introduction of a target vector or DNA fragment.

The gene encoding a target protein, which is linked to the promoter, may be linked to a secretory signal peptide. Due to linkage to the secretory signal peptide, the expressed target protein is secreted to the outside of cells, and therefore the target protein can be isolated from the culture supernatant without destroying the microbial cells. Examples of the secretory signal peptide include signal peptides derived from cellobiohydrolase 1 of *Trichoderma reesei*, alpha-amylase of *Aspergillus oryzae*, glucoamylase of *Rhizopus oryzae* or alpha-factors of *Saccharomyces cerevisiae*.

Examples of the target protein produced by the method of the present invention include oxidoreductases, transferases, hydrolases, lyases, isomerases, ligases or synthetases, glycolytic enzymes, lactate synthetases (LDH etc.), tricarboxylic acid cycle (TCA) enzymes. The target protein may be protein intrinsic to a microorganism cultured by the method of the present invention, or may be foreign protein. Preferred examples of the target protein include enzymes involved in biomass degradation or biomass saccharification. Examples of the enzymes involved in biomass degradation or biomass saccharification include cellulases (e.g. β-endoglucanase, cellobiohydrolase and β-glucosidase), hemicellulases (e.g. endoxylanase, β-xylosidase, arabinofuranosidase, glucuronidase, acetylxylan esterase, mannanase, β-mannosidase and ferulic acid esterase), and xylanase. Of these, cellulases are preferable. The enzyme involved in biomass saccharification or biomass saccharification is preferably an enzyme derived from filamentous fungi, more preferably an enzyme derived from *Trichoderma* fungi.

Examples of the microorganisms cultured in the method of the present invention include bacteria, yeasts and filamentous fungi. Of these, filamentous fungi are preferable. Examples of the filamentous fungi include *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes* and *Trichoderma*. Of these, *Acremonium, Aspergillus, Chrysosporium, Fusarium, Humicola, Myceliophthora, Neurospora, Penicillium, Piromyces, Talaromyces, Thermoascus, Thielavia* and *Trichoderma* are preferable, and *Trichoderma* is more preferable. As *Trichoderma* fungi, *Trichoderma reesei* and variants thereof are preferable. Examples of *Trichoderma reesei* and variants thereof include *Trichoderma reesei* QM9414 strain and variants thereof.

The conditions for culturing a microorganism in the present invention can be appropriately determined conventionally depending on the species of the microorganism and the scale of culture. For example, when the microorganism is filamentous fungi, the culture is maintained at a pH of preferably from 3 to 7, more preferably from 3.5 to 6. The method for measuring the pH of the culture is as described above.

Subsequently, a target protein is collected from the culture. When the protein is secreted in the culture supernatant, the protein can be collected from the culture supernatant. When the protein is contained in cells, the cells are destroyed, and a fraction containing the protein is extracted, and used to collect the protein. The protein can be collected by a method which is commonly used in the field, such as decantation, membrane separation, centrifugation, electrodialysis, use of an ion-exchange resin, distillation, salting-out or a combination thereof. The collected target protein may be further isolated or purified.

When the target protein is secreted in the culture supernatant, the microorganism used for producing the protein in the present invention can be repeatedly used. That is, the microbial cells separated from culture supernatant are collected, and again, the cells are cultured in the presence of glycosylamine as described above, whereby the target protein can be produced again.

The method for producing protein according to the present invention may be a batch method in which culture of a microorganism is alternated with collection of protein accumulated in a culture and replacement of a culture medium, or a semibatch or continuous method in which culture of a microorganism and collection of protein are performed in parallel while the microorganism and a culture medium are partially replaced intermittently or continuously.

As illustrative embodiments of the present invention, the following substances, production methods, uses, methods and the like are disclosed herein. It is to be noted that the present invention is not limited to these embodiments.

[1] A method for producing a protein, comprising culturing a microorganism in the presence of glycosylamine.

[2] The method according to [1], wherein preferably, the culturing a microorganism is performed in the presence of at least one selected from the group consisting of cellulose and cellobiose.

[3] The method according to [2], wherein preferably, the microorganism contains a cellulose-inducing promoter or a cellobiose-inducing promoter, and
the promoter is
preferably a cellulase gene promoter of a filamentous fungus or a xylanase gene promoter a of filamentous fungus,
more preferably a cellulase gene promoter of a *Trichoderma* fungus or a xylanase gene promoter of a *Trichoderma* fungus.

[4] The method according to [3], wherein preferably, a gene encoding the protein is linked downstream of the promoter.

[5] The method according to [4], wherein preferably, the promoter is the cellulase gene promoter of a filamentous fungus, and the protein is an enzyme.

[6] The method according to [4] or [5], wherein the protein is preferably an enzyme, preferably an enzyme involved in biomass degradation or biomass saccharification, more preferably a cellulase,
the enzyme involved in biomass degradation or biomass saccharification is preferably an enzyme derived from a filamentous fungus, more preferably an enzyme derived from a *Trichoderma* fungus, even more preferably a filamentous fungus-derived cellulase, even more preferably a *Trichoderma* fungus-derived cellulase.

[7] The method according to any one of [1] to [6], wherein preferably, the glycosylamine is added to an initial culture medium.

[8] The method according to [7], wherein the amount of the glycosylamine added is preferably 50 g or less, more preferably 30 g or less, even more preferably from 0.5 to 50 g, even more preferably from 0.5 to 30 g, even more preferably from 0.5 to 20 g, even more preferably from 1 to 10 g per L of an initial culture medium.

[9] The method according to any one of [1] to [8], wherein preferably, the glycosylamine is fed to a culture.

[10] The method according to [9], wherein the amount of the glycosylamine fed is preferably 5 g/hr or less, more preferably 4 g/hr or less, even more preferably from 0.005 to 4 g/hr, even more preferably from 0.01 to 3 g/hr per L of an initial culture medium.

[11] The method according to any one of [1] to [10], wherein preferably, the glycosylamine is added to an initial culture medium and fed to a culture, and the content of the glycosylamine in a culture is preferably from 0.5 to 50 g, more preferably from 0.5 to 20 g, even more preferably from 1 to 10 g per L of a culture.

[12] The method according to any one of [9] to [11], wherein preferably, an aqueous solution containing the glycosylamine is fed, and the content of the glycosylamine in the aqueous solution is preferably from 2 to 90 mass %, more preferably from 2 to 50 mass %.

[13] The method according to [12], wherein preferably, the microorganism is cultured while a mixture of glucose and ammonia is fed.

[14] The method according to [13], wherein the mixture is fed in an amount of preferably 8 g/hr or less, more preferably 6 g/hr or less, even more preferably from 0.05 to 8 g/hr, even more preferably from 0.1 to 6 g/hr per L of an initial culture medium in terms of the amount of glucose added to the mixture.

[15] The method according to [13] or [14], wherein by feeding the mixture, a pH of the culture is adjusted to preferably from 3 to 7, more preferably from 3.5 to 6.

[16] The method according to any one of [13] to [15], wherein the mixture contains glucose and ammonia at a mass ratio of preferably from 0.5 to 10:1, more preferably from 2 to 8:1.

[17] The method according to any one of [13] to [16], wherein preferably, the mixture contains glucose in an amount of from 2 to 90 g per 100 mL.

[18] The method according to any one of [12] to [17], wherein a pH of the aqueous solution containing glycosylamine or the mixture of glucose and ammonia is preferably an alkaline pH, more preferably 8 or more, even more preferably 9 or more, even more preferably 10 or more, and preferably 13 or less at 25° C.

[19] The method according to any one of [1] to [18], wherein the glycosylamine is preferably at least one selected from the group consisting of β-D-glucopyranosylamine, β-D-mannopyranosylamine and β-D-galactopyranosylamine, more preferably β-D-glucopyranosylamine.

[20] The method according to any one of [1] to [19], wherein in the culture, the pH of a culture is adjusted to preferably from 3 to 7, more preferably from 3.5 to 6.

[21] The method according to any one of [1] to [20], wherein the microorganism is a filamentous fungus.

[22] The method according to [21], wherein the filamentous fungus is a *Trichoderma* fungus.

[23] The method according to [22], wherein the *Trichoderma* fungus is *Trichoderma reesei*.

[24] The method according to any one of [2] to [23], wherein the microorganism is preferably a filamentous fungus, and the protein is preferably an enzyme involved in biomass degradation or biomass saccharification, more preferably a cellulase.

[25] The method according to [24], wherein the filamentous fungus is preferably a *Trichoderma* fungus.

[26] The method according to [25], wherein the *Trichoderma* fungus is *Trichoderma reesei*.

[27] The method according to any one of [2] to [26], wherein the concentration of cellulose or cellobiose in a culture is preferably from 1 to 15 mass/vol % as a total concentration of cellulose and cellobiose.

[28] The method according to any one of [1] to [27], wherein preferably, the method further comprises collecting the protein from a culture of the microorganism.

EXAMPLES

Hereinafter, the present invention will be described in more detail on the basis of Examples, which should not be construed as limiting the present invention. In Examples below, "%" means "w/v %" unless otherwise specified. The pH of the culture was measured using a pH sensor of F-635 Autoclavable pH Electrode (Broadley-James Corp) or 405-DPAS-SC-K8S pH Sensor (METTLER TOLEDO) provided in a jar fermenter.

Reference Example 1: Synthesis of β-D-Glucopyranosylamine 80 g of D-glucose and 2 g of ammonium chloride were added to 200 mL of methanol, and ammonia gas was introduced into the mixture at 13° C. until the D-glucose and the ammonium chloride were dissolved. Thereafter, the resulting solution was left standing at 4° C. to give a crystal. The obtained crystal was collected by filtration, then washed with methanol, and then dried to give β-D-glucopyranosylamine. The obtained β-D-glucopyranosylamine was used in Examples below.

Comparative Example 1

*Trichoderma reesei* X3AB1 strain (J. Ind. Microbiol. Biotechnol., 2012, 174: 1-9; hereinafter, referred to as X3AB1 strain) was cultured in a cellulose-containing culture medium to produce a protein containing a cellulase. As preculture, 50 mL of a culture medium was added to a 500 mL flask, spores of X3AB1 strain were inoculated at $1 \times 10^5$ cells/mL, and shaking culture was performed at 220 rpm (PRXYg-98R from PRECI CO., LTD.) at 28° C. The culture medium composition was as follows: 1% glucose, 0.14% $(NH_4)_2SO_4$, 0.2% $KH_2PO_4$, 0.03% $CaCl_2 \cdot 2H_2O$, 0.03% $MgSO_4 \cdot 7H_2O$, 0.1% Bacto Peptone (BD Difco), 0.05% Bacto Yeast extract (BD Difco), 0.1% TWEEN® 80 (polysorbate 80), 0.1% Trace element and 50 mM tartrate buffer (pH 4.0). The composition of the Trace element was as follows: 6 mg of $H_3BO_3$, 26 mg of $(NH_4)_6Mo_7O_{24} \cdot 4H_2O$, 100 mg of $FeCl_3 \cdot 6H_2O$, 40 mg of $CuSO_4 \cdot 5H_2O$, 8 mg of $MnCl_2 \cdot 4H_2O$ and 200 mg of $ZnCl_2$ which were diluted to 100 mL with distilled water.

Main culture was performed after 2 days of preculture. The initial culture medium in the main culture contained 10% powder cellulose (KC FLOCK W100 from Nippon Paper Industries Co., Ltd.), and other culture medium components: 0.42% $(NH_4)_2SO_4$, 0.2% $KH_2PO_4$, 0.03% $CaCl_2 \cdot 2H_2O$, 0.03% $MgSO_4 \cdot 7H_2O$, 0.1% Bacto Peptone, 0.05% Bacto Yeast extract, 0.1% TWEEN® 80 (polysorbate 80), 0.1% Trace element and 0.2% Antifoam PE-L. A preculture solution was inoculated in an amount of 10% (v/v %) in a 1 L-volume jar fermenter BMZ-01KP2 (Biott) containing 500 mL of the medium, and culture was performed for 4 days. The jar fermenter was set as follows: temperature: 28° C., aeration rate: 0.5 vvm, pH: 4.5+0.1, and stirring rate: varied so as to maintain DO=3.0 ppm. During the culture, a 10% ammonia aqueous solution was fed to maintain the pH of the culture solution within the above-described predetermined range. On day 2, day 3 or day 4 of culture, samples were taken from the culture solution.

Example 1

Except that β-D-glucopyranosylamine was added in an amount of 0.5% to an initial culture medium in main culture, a microorganism was cultured and samples were taken from a culture solution in the same manner as in Comparative Example 1.

Example 2

Except that during culture in main culture, an 8% β-D-glucopyranosylamine aqueous solution was fed to a culture medium under the conditions shown in Table 1 (β-D-glucopyranosylamine was fed in a total amount of 0.2% per amount of the culture medium added), a microorganism was cultured and samples were taken from a culture solution in the same manner as in Comparative Example 1.

TABLE 1

| Culture time (hr) | Amount added (g/L initial culture medium/hr) |
|---|---|
| 0-15 | 0 |
| 15-63 | 0.6 |

Test 1: Amount of Protein Produced

The culture solutions obtained in Comparative Example 1 and Examples 1 and 2 were centrifuged. Subsequently, fungal cells were separated from the supernatant with a membrane filter 25CS020AN (Advantech). The concentration of protein in the supernatant was measured by the Bradford method. The protein concentration of the supernatant was calculated on the basis of a calibration curve with bovine γ-globulin as standard protein using Quick Start Protein Assay (BioRad) based on the Bradford method, and the protein concentration was defined as an amount of protein produced. FIG. 1 shows relative amounts of protein produced on day 2, day 3 or day 4 of culture in Comparative Example 1 and Examples 1 and 2 against the amount of protein produced on day 3 of culture in Comparative Example 1, which is defined as 100%. The maximum productivity was obtained on day 3 of culture in Example 1 and on day 4 of culture in Example 2, and these values were higher by 20% or more as compared to that in Comparative Example 1. The above results reveal that use of glycosylamine as a culture medium raw material significantly improves the amount of protein produced both when glycosylamine is added to culture medium components in advance and when glycosylamine is fed during culture.

Comparative Example 2

Except that during culture in main culture, a 40% glucose aqueous solution was fed to a culture under conditions shown in Table 2, a microorganism was cultured and samples were taken from a culture solution in the same manner as in Comparative Example 1.

Example 3

Except that during culture in main culture, a 38% glucose/ 2% β-D-glucopyranosylamine aqueous solution was fed to a culture under conditions shown in Table 2, a microorganism was cultured and samples were taken from a culture solution in the same procedure as in Comparative Example 1.

Example 4

Except that during culture in main culture, a 35% glucose/ 5% β-D-glucopyranosylamine aqueous solution was fed to a culture under conditions shown in Table 2, a microorganism was cultured and samples were taken from a culture solution in the same manner as in Comparative Example 1.

TABLE 2

| Culture time (hr) | Amount added (g/L initial culture medium/hr) |
|---|---|
| 0-15 | 0 |
| 15-60 | 2.0 |

Comparative Example 3

Except that during culture in main culture, a 40% glucose aqueous solution was fed to a culture under conditions shown in Table 3, a microorganism was cultured and samples were taken from a culture solution in the same manner as in Comparative Example 1.

Example 5

Except that during culture in main culture, a 38% glucose/ 2% β-D-glucopyranosylamine aqueous solution was fed to a culture under conditions shown in Table 3, a microorganism was cultured and samples were taken from a culture solution in the same manner as in Comparative Example 1.

Example 6

Except that during culture in main culture, a 35% glucose/ 5% β-D-glucopyranosylamine aqueous solution was fed to a culture under conditions shown in Table 3, a microorganism was cultured and samples were taken from a culture solution in the same procedure as in Comparative Example 1.

TABLE 3

| Culture time (hr) | Amount added (g/L initial culture medium/hr) |
|---|---|
| 0-30 | 0 |
| 30-60 | 3.0 |

Test 2: Amount of Protein Produced

For the culture solutions obtained from Comparative Examples 2 and 3 and Examples 3 to 6, the amount of protein produced was measured in the same manner as in Test 1. FIG. 2 shows relative amounts of protein produced at maximum production in Comparative Examples 2 and 3 and Examples 3 to 6 against the amount of protein produced on day 3 of culture in Comparative Example 1, which is defined as 100%. It was confirmed that the protein productivity tended to be improved as the amount of β-D-glucopyranosylamine added in the culture increased. Comparative Example 2 and Examples 3 and 4 were different from Comparative Example 3 and Examples 5 and 6 in timing of starting feeding of the feed liquid and feeding rate of the feed liquid, and comparison of the former with the latter showed that a higher productivity tended to be exhibited when feeding was started early in small batches. The above results reveal that addition of glycosylamine to the culture improves the protein productivity even when glycosylamine is added together with another carbon source such as glucose.

The invention claimed is:

1. A method for producing protein, comprising culturing a microorganism in the presence of glycosylamine,
wherein the microorganism is a *Trichoderma* fungus,
wherein the glycosylamine is at least one selected from the group consisting of β-D-glucopyranosylamine, β-D-mannopyranosylamine and β-D-galactopyranosylamine,
wherein the glycosylamine is continuously fed to the culture during the culturing, and the amount of the glycosylamine that is fed is 5 g/hr or less per liter (L) of an initial culture medium, and
wherein, in the method for producing protein, productivity of the protein is increased as a result of the culturing as compared to productivity of the protein when the *Trichoderma* fungus is cultured under the same conditions but without the glycosylamine.

2. The method according to claim 1, wherein the culturing is performed in the presence of at least one selected from the group consisting of cellulose and cellobiose.

3. The method according to claim 2, wherein the microorganism comprises a promoter selected from a cellulose-inducing promoter and a cellobiose-inducing promoter.

4. The method according to claim 3, wherein a gene encoding a protein is linked downstream of the promoter.

5. The method according to claim 4, wherein the promoter is a cellulase gene promoter of a filamentous fungus, and the protein is an enzyme.

6. The method according to claim 5, wherein the protein is a cellulase.

7. The method according to claim 1, wherein the glycosylamine is added to the initial culture medium.

8. The method according to claim 7, wherein the content of glycosylamine in the culture is from 0.5 to 50 g per L of the culture.

9. The method according to claim 1, wherein the glycosylamine is β-D-glucopyranosylamine.

10. The method according to claim 1, wherein in the culturing, the pH of the culture is adjusted to from 3 to 7.

11. The method according to claim 1, wherein the *Trichoderma* fungus is *Trichoderma reesei*.

12. The method according to claim 1, wherein an enzyme involved in biomass degradation or biomass saccharification is produced.

13. The method according to claim 2, wherein the total concentration of cellulose or cellobiose in the culture of the microorganism is from 1 to 15 mass/vol %.

14. The method according to claim 1, further comprising collecting the protein from the culture of the microorganism.

* * * * *